(12) United States Patent
Okubo et al.

(10) Patent No.: US 8,178,584 B2
(45) Date of Patent: May 15, 2012

(54) WATER-IN OIL EMULSIFIED COMPOSITION

(75) Inventors: Koji Okubo, Tokyo (JP); Yumiko Yamamoto, Tokyo (JP)

(73) Assignee: Kao Corporation, Tokyo (JP)

( * ) Notice: Subject to any disclaimer, the term of this patent is extended or adjusted under 35 U.S.C. 154(b) by 1402 days.

(21) Appl. No.: 10/863,491

(22) Filed: Jun. 9, 2004

(65) Prior Publication Data

US 2005/0163742 A1    Jul. 28, 2005

(30) Foreign Application Priority Data

Jun. 10, 2003    (JP) .................. 2003-165815

(51) Int. Cl.
- *B01F 3/08* (2006.01)
- *B01F 3/00* (2006.01)
- *A01N 33/18* (2006.01)
- *A61K 31/045* (2006.01)
- *A61K 31/01* (2006.01)
- *A61K 31/04* (2006.01)
- *A01N 33/24* (2006.01)
- *A01N 31/00* (2006.01)
- *A01N 27/00* (2006.01)

(52) U.S. Cl. .............. 516/21; 516/9; 514/727; 514/738; 514/740; 514/762; 514/844; 514/937; 514/938; 514/943; 424/78.03; 424/401

(58) Field of Classification Search .............. 516/9, 21; 514/937, 938, 727, 740
See application file for complete search history.

(56) References Cited

U.S. PATENT DOCUMENTS

| | | | |
|---|---|---|---|
| 5,925,365 A | 7/1999 | Yamamoto | |
| 6,348,200 B1 * | 2/2002 | Nakajima et al. | ............ 424/401 |
| 7,846,969 B2 * | 12/2010 | Yamamoto et al. | ........... 514/547 |

FOREIGN PATENT DOCUMENTS

| | | | |
|---|---|---|---|
| CA | 2281430 | * | 12/2000 |
| EP | 0 691 327 | | 1/1996 |
| JP | 10-139651 | | 5/1998 |
| JP | 2000-191496 | | 7/2000 |
| WO | WO 99/29293 | * | 6/1999 |

OTHER PUBLICATIONS

The definition of Dextrin Palmitate (retrieved online on Jul. 15, 2009, via www.cosmeticsdatabase.com).*
Stearic Acid (Beauty) Definition (retrieved online via http://en.mimi.hu/beauty/stearic_acid.html).*
U.S. Appl. No. 12/858,389, filed Aug. 2010, Yamamoto, Y.*

* cited by examiner

*Primary Examiner* — Johann Richter
*Assistant Examiner* — Mei-Ping Chui
(74) *Attorney, Agent, or Firm* — Oblon, Spivak, McClelland, Maier & Neustadt, L.L.P.

(57) ABSTRACT

The present invention relates to a water-in-oil emulsified composition containing a sphingosine represented by the following formula (1):

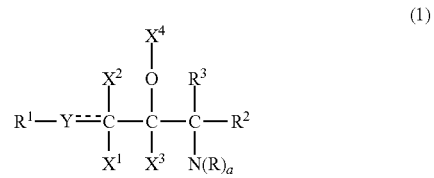

($R^1$ represents a hydrocarbon group optionally having a substituent; Y represents methylene, methine or O; $X^1$, $X^2$ and $X^3$ each represent H, OH or acetoxy group; $X^4$ represents H, acetyl group or the like; $R^2$, $R^3$ each represents H, OH or the like; R represents H, amidino group or the like; and a stands for 2 or 3), (B) a $C_{6-30}$ fatty acid, and
(C) an oil component. This water-in-oil emulsified composition has excellent stability and provides a good feeling to skin upon use.

17 Claims, No Drawings

WATER-IN OIL EMULSIFIED COMPOSITION

FIELD OF THE INVENTION

The present invention relates to a water-in-oil emulsified composition.

BACKGROUND OF THE INVENTION

Water-in-oil emulsified compositions have good affinity with the skin. In addition, they prevent moisture loss from the skin by forming a film on the skin surface, so that they can protect the skin from drying or give treatment effects to the skin. Owing to such characteristics, they are used extensively for cosmetic compositions. In particular, incorporation of a highly viscous oil agent or a solid one as an oil component in the compositions heightens their skin protecting effects, but is accompanied with a defect such as a sticky feeling upon use.

It is a common practice to increase the water content, use a silicone oil as an oil agent or use powder capable of giving a refreshing feeling upon use in order to provide a refreshing sensation without losing the properties of water-in-oil emulsified compositions. When an oil component containing a solid lipid or an oil agent having a particularly high viscosity is emulsified, however, such a measure is not preferred, because it limits the kinds of surfactants to be used as an emulsifier, or requires a large amount of a surfactant, leading to impairment of the affinity with the skin or sometimes causing irritation to the skin. Moreover, such a highly viscous oil agent becomes a cause for disturbing emulsification in a mixture system intended to give a refreshing feeling by increasing the water content or adding a silicone oil.

Various investigations have been made to obtain a water-in-oil emulsified composition providing a good feeling to skin and having high stability in a water-rich system. For example, in Japanese Patent Application Laid-Open No. Hei 10-139651, described is a water-in-oil emulsified cosmetic composition obtained by emulsifying an amide compound having a melting point of from 0 to 50° C. with a nonionic surfactant having an HLB less than 8. It however cannot attain both a good feeling to skin and a stable emulsion.

In Japanese Patent Application Laid-Open No. 2000-191496, described is a cosmetic composition having a salt made of a sphingosine and a $C_{1-17}$ organic acid and having a melting point not greater than that of the sphingosine. Here, in order to improve the miscibility with a highly crystallizable sphingosine, a $C_{1-17}$ organic acid is added to covert the sphingosine into the corresponding cationic salt. This lowers its melting point and facilitates the incorporation of the sphingosine in cosmetic compositions. When the sphingosine salt thus having a reduced melting point is incorporated as a component of an emulsified composition, however, a surfactant must be added to emulsify the salt, so that the resulting composition is not satisfactory from the viewpoint of attaining both good feeling to skin upon use and stability.

SUMMARY OF THE INVENTION

In the present invention, there is provided a water-in-oil emulsified composition containing the following components (A), (B) and (C):

(A) a sphingosine represented by formula (1):

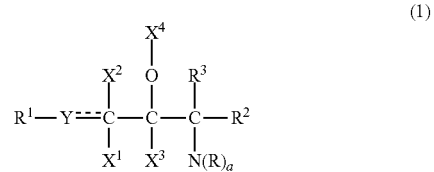

(wherein, $R^1$ represents a linear, branched or cyclic, saturated or unsaturated $C_{4-30}$ hydrocarbon group which may be substituted by a hydroxyl, carbonyl or amino group; Y represents a methylene group, a methine group or an oxygen atom; $X^1$, $X^2$ and $X^3$ each independently represents a hydrogen atom, a hydroxyl group or an acetoxy group, $X^4$ represents a hydrogen atom, an acetyl group or a glyceryl group or forms an oxo group together with the adjacent oxygen atom (with the proviso that when Y represents a methine group, either one of $X^1$ and $X^2$ represents a hydrogen atom and the other one does not exist and when $X^4$ forms an oxo group, $X^3$ does not exist); $R^2$ and $R^3$ each independently represents a hydrogen atom, a hydroxyl group, a hydroxymethyl group or an acetoxymethyl group; R each independently represents a hydrogen atom or an amidino group, or a linear or branched, saturated or unsaturated hydrocarbon group having 1 to 8 carbon atoms in total and optionally having a substituent selected from hydroxyl, hydroxyalkoxy, alkoxy and acetoxy groups; a stands for 2 or 3; and a dashed line indicates a saturated bond or unsaturated bond), (B) a $C_{6-30}$ fatty acid; and (C) an oil component.

DETAILED DESCRIPTION OF THE INVENTION

The present invention relates to a water-in-oil emulsified composition having excellent stability and a good feeling to skin upon use.

The present inventors have found that a water-in-oil emulsified composition having an excellent temporal stability, giving less stickiness and unpleasant feeling to the skin, and providing a good feeling to skin upon use can be obtained by employing a sphingosine, which is a substance inherently existing in the skin, and a fatty acid upon emulsification of an oil component.

Although not wanting to be limited by theory, in the water-in-oil emulsified composition of the present invention, the amine group of a sphingosine represented by formula (1) and a $C_{6-30}$ fatty acid form a salt by acid-base neutralization and the sphingosine thus cationized gains a favorable surface activating capacity, making it possible to create a stable emulsified state. In addition, the sphingosine represented by formula (1) and medium-chain fatty acid function as an activator, so that addition of a surfactant which substantially acts as an emulsifier is not required.

The sphingosine to be used as Component (A) in the present invention is represented by the above-described formula (1).

In the formula, $R^1$ represents a linear, branched or cyclic, saturated or unsaturated $C_{4-30}$ hydrocarbon group which may be substituted by a hydroxyl, carbonyl or amino group, preferably a linear, branched or cyclic, saturated or unsaturated $C_{7-22}$ hydrocarbon group which may be substituted by a hydroxyl group. More preferably, $R^1$ is a linear or branched $C_{10-20}$ alkyl group or a linear or branched $C_{10-20}$ alkyl group having, at a terminal thereof on the Y side, a hydroxyl group.

When it is a branched alkyl group, it preferably has a methyl branched alkyl chain. More specifically, preferred examples include tridecyl, tetradecyl, pentadecyl, hexadecyl, 1-hydroxytridecyl, 1-hydroxypentadecyl, isohexadecyl and isostearyl groups.

Y represents any one of a methylene group ($CH_2$), a methine group (CH) and an oxygen atom.

$X^1$, $X^2$ and $X^3$ each independently represents a hydrogen atom, a hydroxyl group or an acetoxy group, $X^4$ represents a hydrogen atom, an acetyl group, a glyceryl group or a substituent forming an oxo group together with the adjacent oxygen atom. Of these, preferred is the case where at most one of $X^1$, $X^2$ and $X^3$ represents a hydroxyl group, the remaining ones represents a hydrogen atom, and $X^4$ represents a hydrogen atom. When Y represents a methine group, either $X^1$ or $X^2$ represents a hydrogen atom and the other one does not exist. When $X^4$ forms an oxo group, $X^3$ does not exist.

$R^2$ and $R^3$ each independently represents a hydrogen atom, a hydroxyl group, a hydroxymethyl group or an acetoxymethyl group. $R^3$ is preferably a hydrogen atom.

The letter "a" stands for 2 or 3. When a stands for 2, R means $R^4$ or $R^5$ and when a stands for 3, R means $R^4$, $R^5$ or $R^6$.

$R^4$, $R^5$ and $R^6$ each independently represents a hydrogen atom or an amidino group, or a linear or branched, saturated or unsaturated hydrocarbon group having 1 to 8 carbon atoms in total and optionally having a substituent selected from hydroxyl, hydroxyalkoxy, alkoxy and acetoxy groups. As the hydroxyalkoxy group which may be a substituent for the hydrocarbon group, linear or branched $C_{1-7}$ hydrocarbon groups are preferred. As the alkoxy group, linear or branched $C_{1-7}$ alkoxy groups are preferred. Examples of $R^4$, $R^5$ or $R^6$ include a hydrogen atom; linear or branched alkyl groups such as methyl, ethyl, propyl, 2-ethylhexyl and isopropyl; alkenyl groups such as vinyl and allyl; amidino groups; and hydrocarbon groups having 1 to 8 carbon atoms in total and having 1 to 6 substituents selected from hydroxyl group, hydroxyalkoxy groups and alkoxy groups, such as hydroxymethyl, 2-hydroxyethyl, 1,1-dimethyl-2-hydroxyethyl, 2-hydroxypropyl, 2,3-dihydroxypropyl, 2-hydroxy-3-methoxypropyl, 2,3,4,5,6-pentahydroxyhexyl, 1,1-bis(hydroxymethyl)ethyl, 2-(2-hydroxyethoxy)ethyl, 2-methoxyethyl, 1-methyl-2-hydroxyethyl, 3-hydroxypropyl, 3-methoxypropyl, and 1,1-bis(hydroxymethyl)-2-hydroxyethyl.

Of these, a hydrogen atom, a methyl group, and an alkyl group which may be substituted by 1 to 3 substituents selected from hydroxyl group and hydroxyalkoxy groups, such as 2-hydroxyethyl, 1,1-dimethyl-2-hydroxyethyl, 1,1-bis(hydroxymethyl)ethyl, 2-(2-hydroxyethoxy)ethyl are more preferred.

As the sphingosine represented by formula (1), a natural or natural type sphingosine, or derivative thereof represented by the below-described formula (3) (which will hereinafter be described as "natural type sphingosine", collectively), or a pseudo type sphingosine having a sphingosine structure represented by formula (4) (which will hereinafter be described as "pseudo type sphingosine") is preferred.

(I) Natural type sphingosine represented by formula (3):

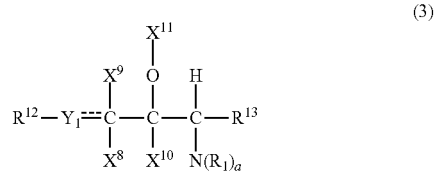

(3)

(wherein, $R^{12}$ represents a linear, branched or cyclic, saturated or unsaturated $C_{7-19}$ hydrocarbon group which may be substituted by a hydroxyl group; $Y_1$ represents a methylene or methine group; $X^8$, $X^9$ and $X^{10}$ each independently represents a hydrogen atom, a hydroxy group or an acetoxy group, $X^{11}$ represents a hydrogen atom or forms an oxo group together with the adjacent oxygen atom (with the proviso that when $Y_1$ represents a methine group, either $X^8$ or $X^9$ represents a hydrogen atom and the other one does not exist, and when $X^{11}$ forms an oxo group, $X^{10}$ does not exist); $R^{13}$ represents a hydroxymethyl or acetoxymethyl group; $R_1$ each independently represents a hydrogen atom or an amidino group, or a linear or branched, saturated or unsaturated hydrocarbon group having 1 to 4 carbon atoms in total and optionally having a substituent selected from hydroxyl, hydroxyalkoxy, alkoxy and acetoxy groups; a stands for 2 or 3; and a dashed line indicates a saturated bond or unsaturated bond).

As $R^{12}$, linear, branched or cyclic, saturated or unsaturated $C_{7-19}$ hydrocarbon groups are preferred, with linear, saturated or unsaturated $C_{13-15}$ hydrocarbon groups being more preferred. It is preferred that a stands for 2 and $R_1$s each independently represents a hydrogen atom or a linear or branched $C_{1-4}$ alkyl group.

Specific examples of the natural type sphingosine represented by formula (3) include natural sphingosine, dihydrosphingosine, phytosphingosine, sphingadienine, dehydrosphingosine, and dehydrophytosphingosine and N-alkyl derivatives (N-methyl derivatives) thereof.

As these sphingosines, natural (D(+) form) optically active derivatives, unnatural (L(−) form) optically active derivatives or a mixture thereof may be used. The relative configuration of these compounds may be any one of the configuration of a natural form, that of an unnatural form and that of their mixture.

Moreover, PHYTOSPHINGOSINE (listed in INCI; 8th Edition) and those represented by the below-described formulas are preferred.

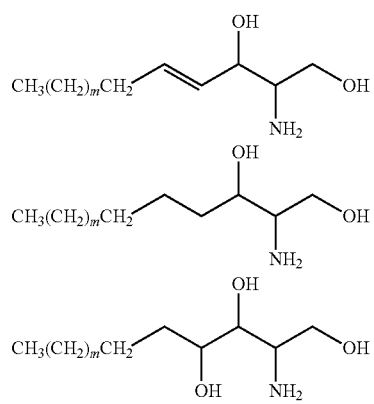

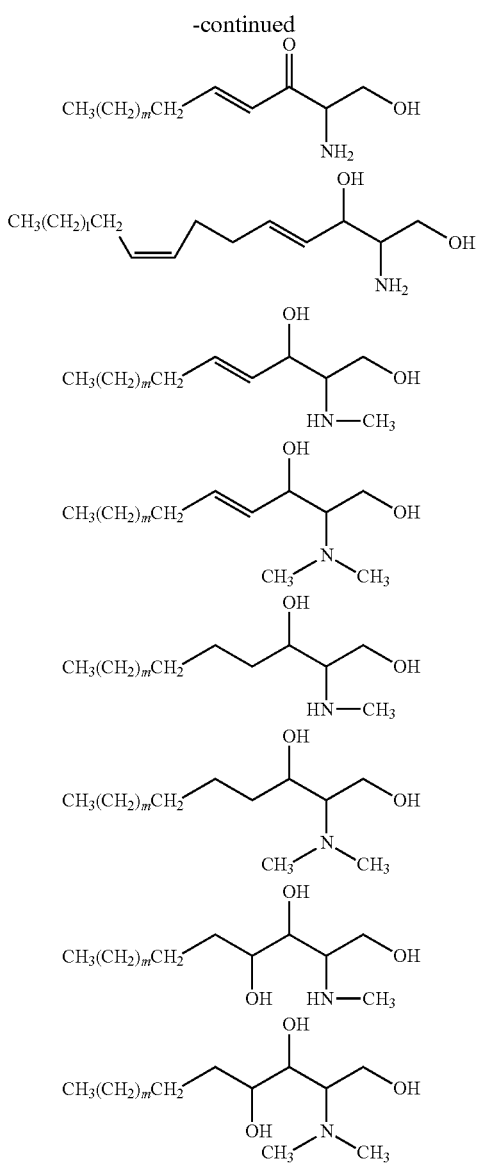

(wherein, m stands for 5 to 17 and l stands for 1 to 13).

They may be an extract from natural sphingosine or a synthesized product thereof. A commercially available one can also be used.

Examples of the commercially available natural type sphingosine include D-Sphingosine (4-Sphingenine) (product of SIGMA-ALDRICH), DS-phytosphingosine (product of DOOSAN) and phytosphingosine (product of Cosmo Ferm).

(II) Pseudo type sphingosines represented by the following formula (4)

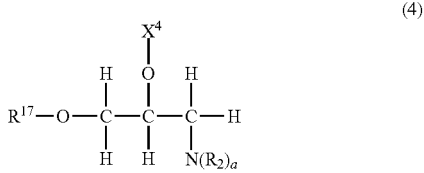

(wherein, $R^{17}$ represents a linear, branched or cyclic, saturated or unsaturated $C_{10-22}$ hydrocarbon group which may be substituted by a hydroxyl group; $X^4$ represents a hydrogen atom, an acetyl group or a glyceryl group; $R_2$ each independently represents a hydrogen atom or an amidino group, or a linear or branched, saturated or unsaturated hydrocarbon group having 1 to 8 carbon atoms in total and optionally having a substituent selected from hydroxyl, hydroxyalkoxy, alkoxy and acetoxy groups, and a stands for 2 or 3).

As $R^{17}$, iso-branched alkyl groups having 14 to 20 carbon atoms are preferred, with an isostearyl group being more preferred. Still more preferred is an isostearyl group available by using as a raw material oil an isostearyl alcohol derived from a by-product of a dimer acid preparation using a fatty acid derived from an animal or plant oil.

When a stands for 2, $R_2$ means $R^{18}$ or $R^{19}$, while when a stands for 3, $R_2$ means $R^{18}$, $R^{19}$ or $R^{20}$.

Examples of $R^{18}$, $R^{19}$ or $R^{20}$ include a hydrogen atom; linear or branched alkyl groups such as methyl, ethyl, propyl, 2-ethylhexyl and isopropyl; alkenyl groups such as vinyl and allyl; an amidino group; and alkyl groups having 1 to 8 carbon atoms in total and having a substituent selected from hydroxyl, hydroxyalkoxy and alkoxy groups, such as hydroxymethyl, 2-hydroxyethyl, 1,1-dimethyl-2-hydroxyethyl, 2-hydroxypropyl, 2,3-dihydroxypropyl, 2-hydroxy-3-methoxypropyl, 2,3,4,5,6-pentahydroxyhexyl, 1,1-bis(hydroxymethyl)ethyl, 2-(2-hydroxyethoxy)ethyl, 2-methoxyethyl, 1-methyl-2-hydroxyethyl, 3-hydroxypropyl, 3-methoxypropyl, and 1,1-bis(hydroxymethyl)-2-hydroxyethyl.

A secondary amine having as either $R^{18}$ or $R^{19}$ a hydrogen atom and as the other one a 2-hydroxyethyl, 1,1-dimethyl-2-hydroxyethyl, 1,1-bis(hydroxymethyl)ethyl or 2-(2-hydroxyethoxy)ethyl group is still more preferred.

As the pseudo type sphingosine, that having as $R^{17}$ an isostearyl group, as $X^4$ a hydrogen atom, $R^{18}$ a hydrogen atom, and as $R^{19}$ an alkyl group having 1 to 3 substituents selected from hydroxyl and hydroxyalkoxy groups, such as 2-hydroxyethyl, 1,1-bis(hydroxymethyl)ethyl, 1,1-dimethyl-2-hydroxyethyl or 2-(2-hydroxyethoxy)ethyl group is preferred.

The following pseudo type sphingosines (i) to (iv) are specific examples of the pseudo type sphingosine.

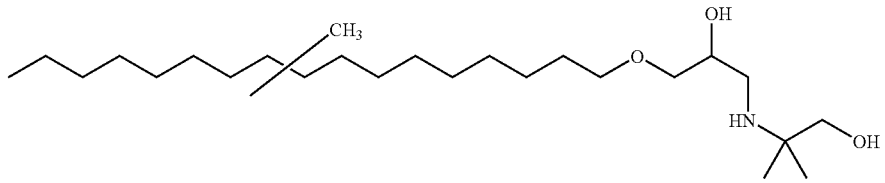

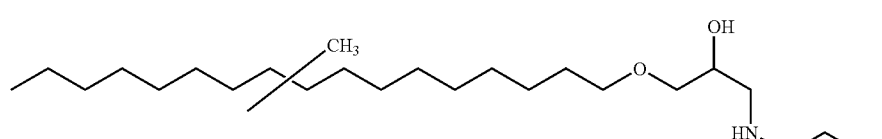

(ii)

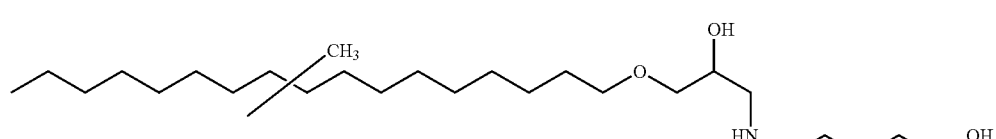

(iii)

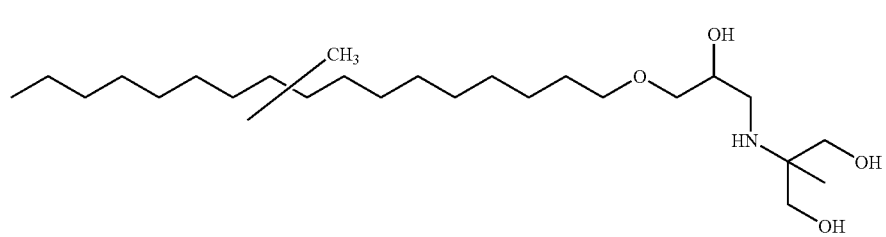

(iv)

As Component (A), two or more compounds may be used in combination. The content of Component (A) in the composition of the present invention is preferably from 0.001 to 10 weight %, more preferably from 0.005 to 3 weight %, still more preferably from 0.01 to 3 weight %.

The fatty acid as Component (B) to be used in the present invention forms its salt with the amine group of the sphingosine by acid-base neutralization and the sphingosine cationized by this reaction acquires a function as an activator. The salt of the sphingosine can be determined by infrared absorption spectroscopy or proton nuclear magnetic resonance spectroscopy which has conventionally been used for identification of the structure of a compound.

The chain length of the fatty acid is selected, based on the kind of oil components to be emulsified, and viscosity of the emulsified composition. For example, a stable emulsion state can be attained by using a short chain fatty acid when a relatively low viscous emulsified composition in the milky liquid form is prepared; and by using a long chain fatty acid when a highly viscous emulsified composition in the cream form is prepared.

The fatty acid as Component (B) has from 6 to 30 carbon atoms. In view of the stability and feeling upon use of the emulsified composition, saturated or unsaturated $C_{8-22}$ fatty acids are more preferred. When a $C_{6-30}$ fatty acid is used, a stable water-in-oil emulsified composition is available even if the oil component is composed of plural ones. Specific examples include saturated fatty acids such as caproic acid, caprylic acid, capric acid, lauric acid, myristic acid, palmitic acid, stearic acid, eicosanoic acid and docosanoic acid, and unsaturated fatty acids such as oleic acid, linoleic acid, linolenic acid, ricinoleic acid, eicosapentaenoic acid and docosahexanoeic acid.

Of these, saturated $C_{12-18}$ fatty acids are preferred from the viewpoint of good feeling to skin upon use, with myristic acid and palmitic acid being more preferred.

As Component (B), two or more fatty acids may be used in combination. The content of Component (B) in the composition of the present invention preferably ranges from 0.001 to 10 weight %, more preferably from 0.005 to 6 weight %, still more preferably from 0.01 to 3 weight %.

Component (B) is added to cationize the amine group of the sphingosine preferably (A) in an amount of at least 0.3 mole per mole of Component (A). For improvement of the emulsifying property, addition of from 0.3 to 5 moles is more preferred, with addition of from 0.5 to 3 moles being still more preferred.

As the oil component (C) to be used in the present invention, a synthetic or natural oil component which is ordinarily employed for cosmetics, and preferably is in the solid, semi-solid or liquid form at 25° C. can be added. The oil component forms a continuous phase in the emulsified composition. From the viewpoint of emulsion stability with the passage of time, an oil component composed mainly of a nonpolar liquid oil is preferred.

Examples of the non-polar liquid oil (25° C.) include plant oils such as jojoba oil; animal oils such as liquid lanolin; hydrocarbon oils such as liquid paraffin and squalane; silicone oils such as dimethylpolysiloxane, dimethylcyclopolysiloxane, methylphenylpolysiloxane, methylhydrogenpolysiloxane, and higher alcohol modified organopolysiloxane; and fluorine oils such as fluoropolyether and perfluoroalkyl ether silicone. The content of the nonpolar oil is preferably 50 weight % or more, more preferably 70 weight % or more, still more preferably 90 weight % or more in the whole oil component.

Examples of the liquid oil component other than the nonpolar oil include fatty acid esters such as diisostearyl malate, octyldodecyl lactate, isotridecyl isononanoate, isopropyl isostearate and octyldodecyl myristate; ester oils made of a fatty acid and an alcohol such as neopentyl glycol dicaprate; and ester oils such as amino acid derivatives.

Examples of the solid or semi-solid oil component include plant oils such as jojoba wax; alkyl glyceryl ethers such as glycerin monostearyl ether and glycerin monocetyl ether; waxes such as petrolatum, lanolin, ceresin, microcrystalline wax, carnauba wax and candelilla wax; and intercellular lipids such as ceramides or derivatives thereof, cholesterol or derivatives thereof, and $C_{12-18}$ fatty acids.

In the present invention, addition of an intercellular lipid such as a ceramide or derivative thereof, cholesterol or derivative thereof, or $C_{12-18}$ fatty acid as the oil component is preferred in consideration of the feeling when the emulsified composition is applied to the skin. As the ceramide or derivative thereof, the addition of a ceramide represented by the following formula (2) is preferred.

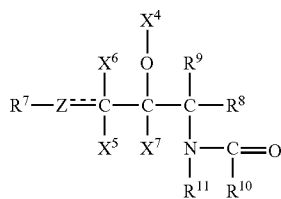

(2)

(wherein, $R^7$ represents a linear, branched or cyclic, saturated or unsaturated $C_{4-30}$ hydrocarbon group which may be substituted by a hydroxyl, carbonyl or amino group, or a hydrogen atom; Z represents a methylene group, a methine group or an oxygen atom; $X^5$, $X^6$ and $X^7$ each independently represents a hydrogen atom, a hydroxyl group or an acetoxy group, $X^4$ represents a hydrogen atom, an acetyl group or a glyceryl group, or forms an oxo group together with the adjacent oxygen atom (with the proviso that when Z represents a methine group, either one of $X^5$ and $X^6$ represents a hydrogen atom and the other one does not exist and when $X^4$ forms an oxo group, $X^7$ does not exist); $R^8$ and $R^9$ each independently represents a hydrogen atom, a hydroxyl group, a hydroxymethyl group or an acetoxymethyl group; $R^{10}$ represents a linear, branched or cyclic, saturated or unsaturated $C_{5-60}$ hydrocarbon group which may be substituted by a hydroxyl, carbonyl or amino group and may have an ether bond, ester bond or amide bond in the main chain; $R^{11}$ represents a hydrogen atom, or a linear or branched, saturated or unsaturated hydrocarbon group having 1 to 30 carbon atoms in total and optionally having a substituent selected from hydroxyl, hydroxyalkoxy, alkoxy and acetoxy groups (with the proviso that when $R^7$ represents a hydrogen atom and Z represents an oxygen atom, $R^{11}$ represents a hydrocarbon group having 10 to 30 carbon atoms in total and when $R^7$ represents a hydrocarbon group, $R^{11}$ represents a hydrocarbon group having 1 to 8 carbon atoms in total); and a dashed line indicates a saturated bond or unsaturated bond).

In the formula, $R^7$ represents a linear, branched or cyclic, saturated or unsaturated $C_{4-30}$ hydrocarbon group which may be substituted by a hydroxyl, carbonyl or amino group, preferably a linear, branched or cyclic, saturated or unsaturated $C_{7-22}$ hydrocarbon group which may be substituted by a hydroxyl group, or a hydrogen atom.

Z represents a methylene group, a methine group or an oxygen atom.

$X^5$, $X^6$ and $X^7$ each independently represents a hydrogen atom, a hydroxyl group or an acetoxy group. It is preferred that at most one of $X^5$, $X^6$ and $X^7$ represents a hydroxyl group and the remaining two represents a hydrogen atom. When Z represents a methine group, either $X^5$ or $X^6$ represents a hydrogen atom and the other one does not exist. $X^4$ is preferably a hydrogen atom or a glyceryl group.

$R^8$ and $R^9$ each represents a hydrogen atom, a hydroxyl group, a hydroxymethyl group or an acetoxymethyl group. $R^8$ preferably represents a hydrogen atom or a hydroxymethyl group, while $R^9$ preferably represents a hydrogen atom.

$R^{10}$ represents a linear, branched or cyclic, saturated or unsaturated $C_{5-60}$ hydrocarbon group which may be substituted by a hydroxyl, carboxy or amino group and may have an ether bond, ester bond or amide bond in its main chain. $R^{10}$ preferably represents a linear, branched or cyclic, saturated or unsaturated $C_{5-35}$ hydrocarbon group which may be substituted by a hydroxyl or amino group, or the above-described hydrocarbon group having, to the ω position thereof, a linear, branched or cyclic, saturated or unsaturated $C_{8-22}$ fatty acid, which may be substituted by a hydroxyl group, ester-bound or amide-bound. As the fatty acid to be bound, isostearic acid, 12-hydroxystearic acid or linoleic acid is preferred.

$R^{11}$ represents a hydrogen atom, or a linear or branched, saturated or unsaturated hydrocarbon group having 1 to 30 carbon atoms in total and optionally having a substituent selected from hydroxyl, hydroxyalkoxy, alkoxy and acetoxy groups. When $R^7$ represents a hydrogen atom and Z represents an oxygen atom, $R^{11}$ is a hydrocarbon group having 10 to 30 carbon atoms in total. When $R^7$ represents a hydrocarbon group, $R^{11}$ represents a hydrocarbon group having 1 to 8 carbon atoms in total. Of these, a hydrogen atom and hydrocarbon groups which have 1 to 8 carbon atoms in total and may have 1 to 3 substituents selected from hydroxyl, hydroxyalkoxy and alkoxy groups are preferred. As the hydroxyalkoxy and alkoxy groups, those having 1 to 7 carbon atoms are preferred.

As the ceramide represented by formula (2), those represented by the following formula (5) or (6) are preferred.

(I) Natural or natural type ceramide, or derivative thereof represented by formula (5) (which will hereinafter be called "natural type ceramide")

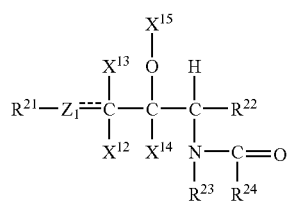

(5)

(wherein, $R^{21}$ represents a linear, branched or cyclic, saturated or unsaturated $C_{7-19}$ hydrocarbon group which may be substituted by a hydroxyl group; $Z_1$ represents a methylene or methine group; $X^{12}$, $X^{13}$ and $X^{14}$ each independently represents a hydrogen atom, a hydroxyl group or an acetoxy group; $X^{15}$ represents a hydrogen atom or forms an oxo group together with the adjacent oxygen atom (with the proviso that when $Z_1$ represents a methine group, either $X^{12}$ or $X^{13}$ represents a hydrogen atom and the other one does not exist, and when $X^{15}$ represents an oxo group, $X^{14}$ does not exist); $R^{22}$ represents a hydroxymethyl or acetoxymethyl group; R represents a hydrogen atom or a $C_{1-4}$ alkyl group; $R^{24}$ represents a linear, branched or cyclic, saturated or unsaturated $C_{5-30}$ hydrocarbon group which may be substituted by a hydroxyl group, or the above-described hydrocarbon group having, to the ω position thereof, a linear or branched, saturated or unsaturated $C_{8-22}$ fatty acid, which may be substituted by a hydroxyl group, ester-bound; and a dashed line indicates a possible unsaturated bond).

Preferred are compounds having as $R^{21}$ a linear $C_{7-19}$, more preferably $C_{13-15}$ alkyl group, and as $R^{24}$ a linear $C_{9-27}$ alkyl group which may be substituted by a hydroxyl group or a linear $C_{9-27}$ alkyl group having linoleic acid ester-bound thereto. $X^{15}$ preferably represents, a hydrogen atom or forms an oxo group, together with an oxygen atom. As $R^{24}$, a tricosyl group, a 1-hydroxypentadecyl group, a 1-hydroxytricosyl group, a heptadecyl group, a 1-hydroxyundecyl group or a nonacosyl group having linoleic acid ester-bound to the ω position thereof is preferred.

Specific examples of the natural type ceramides include Ceramide Types 1 to 7 obtained by amidation of sphingosine, dihydrosphingosine, phytosphingosine or sphingadienine (for example, FIG. 2 of J. Lipid Res., 24: 759 (1983), and pig and human ceramides as described in FIG. 4 of J. Lipid Res., 35: 2069 (1994)).

The N-alkyl derivatives (for example, N-methyl derivative) of these ceramides are also included.

As these ceramides, natural (D(−) form) optically active derivatives, unnatural (L(+) form) optically active derivatives or a mixture thereof may be used. The relative configuration of these compounds may be any one of the configuration of a natural form, that of an unnatural form and that of their mixture. More preferred ones are compounds such as CERAMIDE 1, CERAMIDE 2, CERAMIDE 3, CERMIDE 5, and CERAMIDE 6II (listed in INCI, 8th Edition) and those represented by the following formulas.

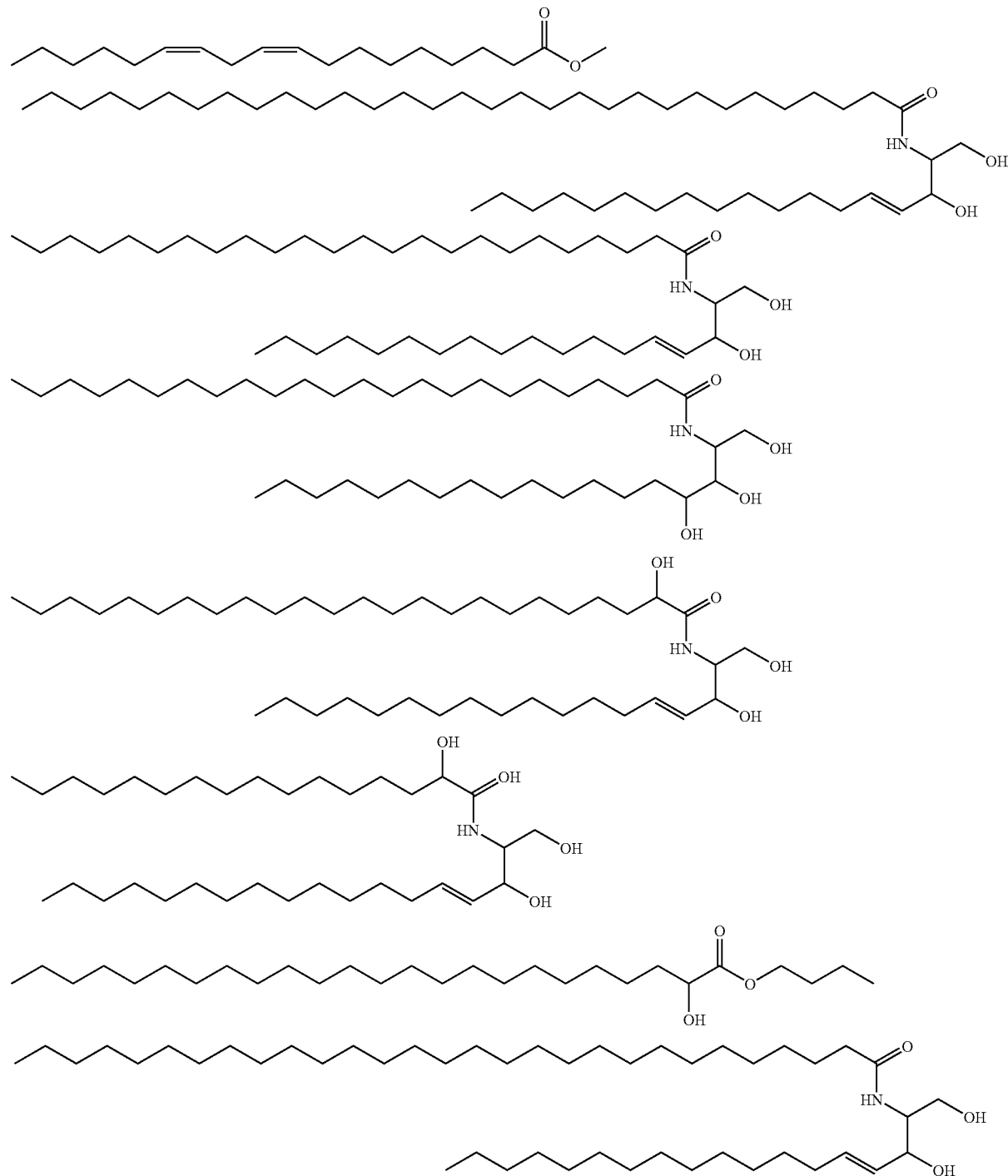

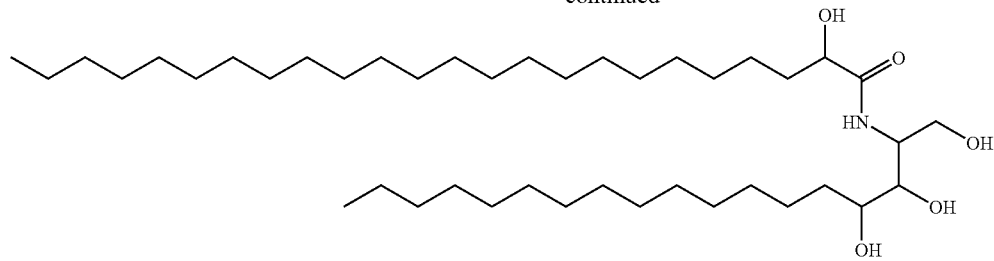

They may be either compounds extracted from natural ceramides or synthesized ones thereof. Commercially available ones are also usable.

Examples of the commercially available natural type ceramides include Ceramide I, Ceramide III, Ceramide IIIA, Ceramide IIIB, Ceramide IIIC, and Ceramide VI (each, product of Cosmo Ferm), Ceramide TIC-001 (product of Takasago International Corp.), CERAMIDE II (product of Quest International), DS-Ceramide VI, DS-CLA-Phytoceramide, C6-Phytoceramide and DS-ceramide Y3S (product of DOOSAN), and CERAMIDE 2 (product of Sederma).

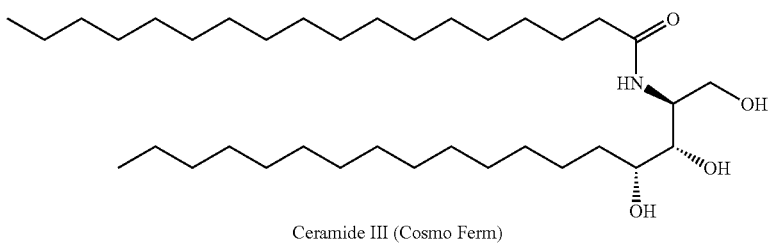

Ceramide III (Cosmo Ferm)

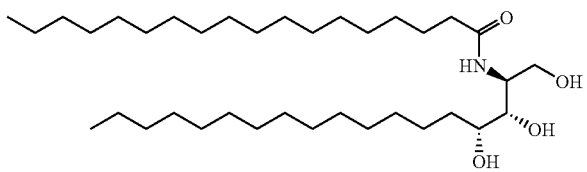

Ceramide IIIB (Cosmo Ferm)

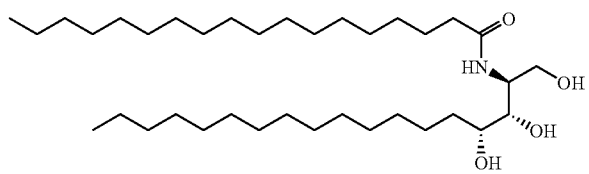

Ceramide IIIA (Cosmo Ferm)

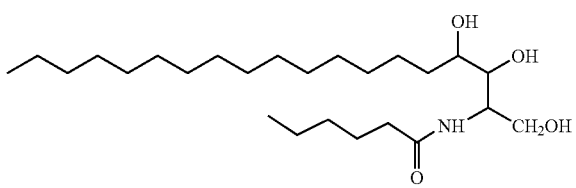

Phytoceramide (DOOSAN)

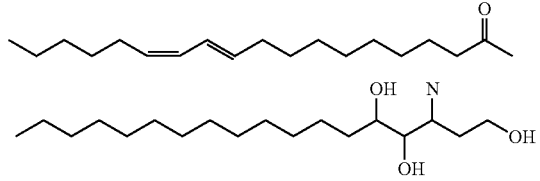

DS-CLA-Phytoceramide (DOOSAN)

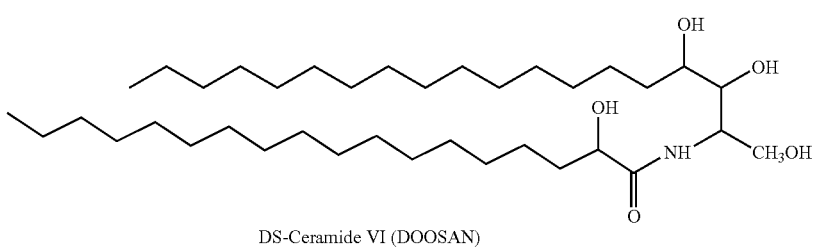

DS-Ceramide VI (DOOSAN)

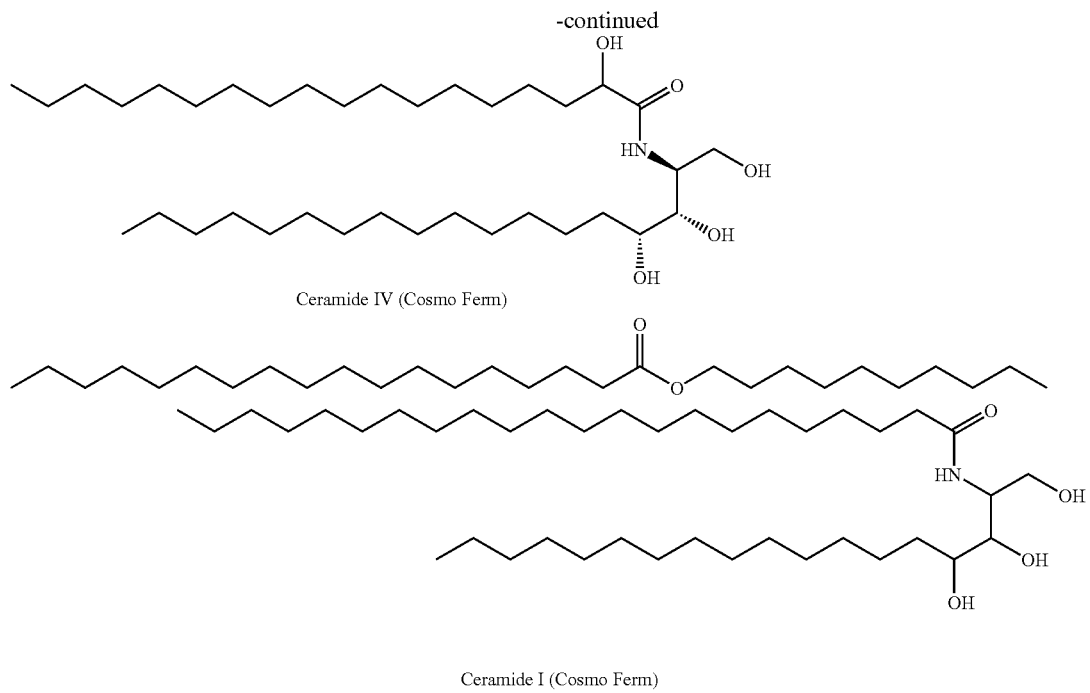

Ceramide IV (Cosmo Ferm)

Ceramide I (Cosmo Ferm)

(II) Pseudo type ceramides represented by the following formula (6)

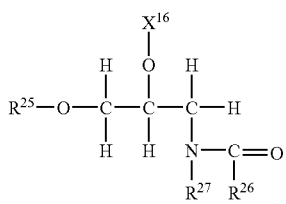

(6)

(wherein, $R^{25}$ represents a linear, branched or cyclic, saturated or unsaturated $C_{10\text{-}22}$ hydrocarbon group which may be substituted by a hydroxyl group, or a hydrogen atom; $X^{16}$ represents a hydrogen atom, an acetyl group or a glyceryl group; $R^{26}$ represents a linear, branched or cyclic, saturated or unsaturated $C_{5\text{-}22}$ hydrocarbon group which may be substituted by a hydroxyl or amino group, or the above-described hydrocarbon group having, to the ω position thereof, a linear or branched, saturated or unsaturated $C_{8\text{-}22}$ fatty acid, which may be substituted by a hydroxyl group, ester-bound; and $R^{27}$ represents a hydrogen atom or an alkyl group which has 1 to 30 carbon atoms in total and may have been substituted by a hydroxyl, hydroxyalkoxy, alkoxy or acetoxy group).

Preferred as $R^{26}$ are a nonyl group, a tridecyl group, a pentadecyl group, an undecyl group having linoleic acid ester-bound to the ω position thereof, a pentadecyl group having linoleic acid ester-bound to the ω position thereof, a pentadecyl group having 12-hydroxystearic acid ester-bound to the ω position thereof, and an undecyl group having methyl-branched isostearic acid amide-bound to the ω position thereof.

$R^{27}$ is preferably an alkyl group which has 10 to 30, preferably 12 to 20 carbon atoms in total, and may be substituted by a hydroxyl, hydroxyalkoxy, alkoxy or acetoxy group when $R^{25}$ represents a hydrogen atom; or a hydrogen atom or an alkyl group which has 1 to 8 carbon atoms in total and may be substituted by a hydroxyl, hydroxyalkoxy, alkoxy or acetoxy group when $R^{25}$ represents a linear, branched or cyclic, saturated or unsaturated $C_{10\text{-}22}$ hydrocarbon group which may be substituted by a hydroxyl group. The hydroxyalkoxy or alkoxy group as $R^{27}$ preferably has 1 to 7 carbon atoms.

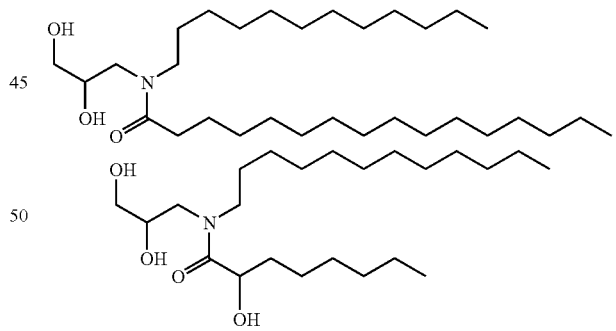

As the pseudo type ceramide of formula (6), those having as $R^{25}$ a hexadecyl group, as $X^{16}$ a hydrogen atom, as $R^{26}$ a pentadecyl group, and as $R^{27}$ a hydroxyethyl group; those having as $R^{25}$ a hexadecyl group, as $X^{16}$ a hydrogen atom, as $R^{26}$ a nonyl group, and as $R^{27}$ a hydroxyethyl group; or those having as $R^{25}$ a hexadecyl group, as $X^{16}$ a glyceryl group, as $R^{26}$ a tridecyl group, and as $R^{27}$ a 3-methoxypropyl group are preferred, with those of formula (6) having as $R^{25}$ a hexadecyl group, as $X^{16}$ a hydrogen atom, as $R^{26}$ a pentadecyl group, and as $R^{27}$ a hydroxyethyl group being more preferred.

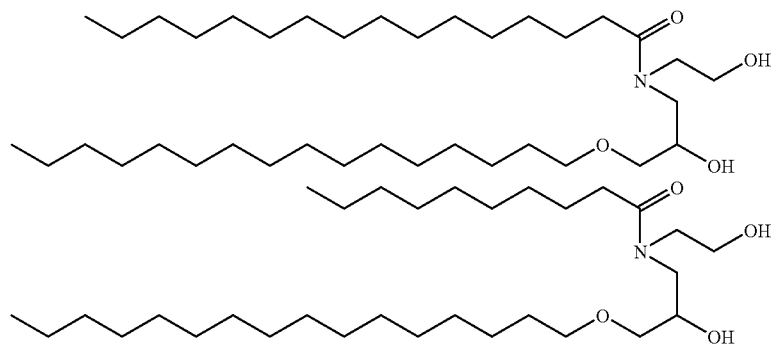

The ceramide is added preferably in an amount of from 0.0001 to 50 weight %, preferably from 0.01 to 20 weight %, more preferably from 0.01 to 15 weight % in the oil component.

As Component (C), two or more of these ceramides may be used in combination. The content of Component (C) in the composition of the present invention is preferably from 20 to 99 weight %, more preferably from 30 to 93 weight %, still more preferably from 40 to 85 weight %.

The amount of water contained in the water-in-oil emulsified composition of the present invention is preferably from 1 to 80 weight %, more preferably from 7 to 70 weight %, still more preferably from 15 to 60 weight %, in the whole composition.

In the water-in-oil emulsified cosmetic composition of the present invention, it is possible to incorporate other components ordinarily employed for cosmetic compositions, for example, a humectant such as 1,3-butylene glycol, propylene glycol, dipropylene glycol, glycerin, diglycerin, sorbitol, maltitol, polyethylene glycol, glycine betaine, xylitol, trehalose, urea or amino acid; a water soluble thickener such as xanthan gum, hydroxyethyl cellulose, methyl cellulose or hydroxypropyl guar gum; a medicinal component such as allantoin or tocopherol acetate; an organic powder such as cellulose powder, nylon powder, crosslinked silicone powder, crosslinked methylpolysiloxane, porous cellulose powder, or porous nylon powder; an inorganic powder such as silica anhydride, zinc oxide or titanium oxide; cool-feel imparting agent such as menthol or camphor; pH buffer, antioxidant, ultraviolet absorber, antiseptic, perfume, bactericide or colorant.

The water-in-oil emulsified composition can be prepared by dissolving Components (A) to (C) under heat, adding water to the resulting solution and then, emulsifying the mixture.

The water-in-oil emulsified composition of the present invention can be used as a cosmetic or pharmaceutical. Upon use as a cosmetic, cosmetic emulsion, cream, foundation or hair cream is preferred, with a cosmetic cream being more preferred.

EXAMPLES

Examples 1 to 8, Comparative Examples 1 to 4

The water-in-oil emulsified compositions having the composition as shown in Tables 1 and 2 were prepared by the below-described process. The resulting emulsified compositions were evaluated for stability and feeling upon use (ease of spreading, non-stickiness). The results are shown collectively in Tables 1 and 2.
(Preparation Process)

Oil phase components (Components (A) to (C), etc.) were stirred under heat at 80 to 90° C. to dissolve. An aqueous phase component was then added to the resulting solution while stirring the mixture uniformly. After further stirring, the reaction mixture was cooled to obtain a water-in-oil emulsified composition.
(Evaluation Method)
(1) Stability:

Each emulsified composition was allowed to stand for 1 week under three conditions, that is, 50° C., room temperature (25° C.) and −5° C. and evaluated visually for its appearance in accordance with the below-described criteria.
A: Neither emulsion separation nor change in appearance is recognized.
B: Emulsion separation is not recognized, but there is a little change in appearance.
C: Both emulsion separation and a great change in appearance are recognized.
2) Feeling Upon Use "Ease of spreading" and "non-stickiness" of each emulsified composition upon use were organoleptically evaluated by a panel of 10 experts and rated in accordance with the following criteria.
A: At least nine experts rated it as favorable (good).
B: Seven to Eight experts rated it as favorable (good).
C: Six or less experts rated it as favorable (good).

TABLE 1

| | Component (weight %) | Example | | | | | Comp. Ex. | |
| | | 1 | 2 | 3 | 4 | 5 | 1 | 2 |
|---|---|---|---|---|---|---|---|---|
| A | (1) Pseudo type sphingosine (ii) | 0.2 | 0.2 | 0.2 | 0.2 | | 0.2 | |
| | (2) Sphingosine | | | | | 0.2 | | |
| B | (3) Lauric acid | 0.3 | | | | | | |
| | (4) Myristic acid | | 0.3 | | | 0.3 | | |
| | (5) Palmitic acid | | | 0.25 | | | | |

TABLE 1-continued

|  | Component (weight %) | Example 1 | Example 2 | Example 3 | Example 4 | Example 5 | Comp. Ex. 1 | Comp. Ex. 2 |
|---|---|---|---|---|---|---|---|---|
|  | (6) Stearic acid |  |  |  | 0.3 |  |  |  |
|  | (7) Butyric acid |  |  |  |  |  | 0.3 |  |
| C | (8) Pseudo type ceramide *1 | 7.0 | 7.0 | 7.0 | 7.0 | 7.0 | 7.0 | 7.0 |
|  | (9) Squalane | 10.5 | 10.5 | 10.5 | 10.5 | 10.5 | 10.5 | 10.5 |
|  | (10) Dimethylpolysiloxane (6cs) | 8.5 | 8.5 | 8.5 | 8.5 | 8.5 | 8.5 | 8.5 |
|  | (11) Dimethylcyclopolysiloxane (D5) | 10.0 | 10.0 | 10.0 |  | 10.0 | 10.0 | 10.0 |
|  | (12) Isostearyl glyceryl ether |  | 1.0 | 1.0 | 1.0 | 1.0 | 1.0 | 1.0 |
|  | (13) Triisostearic acid polyoxyethylene hydrogenated castor oil (15 E.O.) |  |  |  |  |  |  | 1..5 |
| Aqueous phase | (14) Glycerin | 17.0 | 17.0 |  | 17.0 | 17.0 | 17.0 | 17.0 |
|  | (15) 1,3-Butylene glycol | 3.0 | 3.0 |  | 3.0 | 3.0 | 3.0 | 3.0 |
|  | (16) Purified water | Balance | Balance | Balance | Balance | Balance | Balance | Balance |
| Evaluation | Stability: 50° C. | A | A | A | A | A | C | B |
|  | : 25° C. | A | A | A | A | A | C | B |
|  | : −5° C. | A | A | A | A | A | C | B |
|  | Feeling upon use: |  |  |  |  |  |  |  |
|  | ease of spreading | A | A | A | A | A | B | C |
|  | Non-stickiness | A | A | A | A | A | B | C |

*1: Pseudo type ceramide of formula (6) in which $R^{25}$ represents a hexadecyl group, $X^{16}$ represents a hydrogen atom, $R^{26}$ represents a pentadecyl group and $R^{27}$ represents a hydroxyethyl group.

TABLE 2

|  | Component (weight %) | Example 6 | Example 7 | Example 8 | Comp. Ex. 3 | Comp. Ex. 4 |
|---|---|---|---|---|---|---|
| A | (1) Pseudo sphingosine (ii) | 2.0 | 1.0 |  | 1.0 |  |
|  | (2) Sphingosine |  |  | 1.0 |  |  |
| B | (3) Myristic acid |  | 1.5 |  |  | 1.5 |
|  | (4) Palmitic acid | 3.0 |  | 1.5 |  |  |
| C | (5) Pseudo type ceramide *1 |  | 3.0 | 3.0 | 3.0 | 3.0 |
|  | (6) Squalane | 33.0 | 33.0 | 33.0 | 33.0 | 33.0 |
|  | (7) Dimethylpolysiloxane (6cs) | 10.0 | 10.0 | 10.0 | 10.0 | 10.0 |
|  | (8) Dimethylcyclopolysiloxane (D5) | 10.0 | 10.0 | 10.0 | 10.0 | 10.0 |
|  | (9) Dextrin palmitate | 2.0 | 1.0 | 1.0 | 1.0 | 1.0 |
|  | (10) Paraffin |  | 0.5 | 0.5 | 0.5 | 0.5 |
| Aqueous phase | (11) Glycerin | 16.0 | 16.0 | 16.0 | 16.0 | 16.0 |
|  | (12) 1,3-Butylene glycol | 3.0 | 3.0 | 3.0 | 3.0 | 3.0 |
|  | (13) Purified water | Balance | Balance | Balance | Balance | Balance |
| Evaluation | Stability: 50° C. | B | A | A | C | C |
|  | : 25° C. | B | A | A | C | C |
|  | : −5° C. | B | A | A | C | C |
|  | Feeling upon use: |  |  |  |  |  |
|  | Ease of spreading | B | B | B | B | C |
|  | Non-stickiness | B | B | B | B | C |

Example 9

Cream

The cream having the composition as shown in Table 3 was prepared in the below-described process. The resulting cream had good stability and a good feeling to the skin upon use (ease of spreading, nonstickiness).

(Preparation Process)

Components (1) to (7) are dissolved at 80° C., followed by stirring uniformly to prepare an oil phase. Components (8) to (11) are dissolved at 80° C., followed by stirring uniformly to prepare an aqueous phase. The aqueous phase is added to the oil phase and the mixture is stirred uniformly at 80° C. The reaction mixture is then cooled to room temperature, whereby a cream is obtained.

TABLE 3

|  | (Component) | (weight %) |
|---|---|---|
| (1) | Pseudo type ceramide *1 | 7.0 |
| (2) | Pseudo type sphingosine | 0.2 |
| (3) | Myristic acid | 0.3 |
| (4) | Dextrin palmitate | 1.0 |
| (5) | Squalane | 9.0 |
| (6) | Dimethylpolysiloxane (6 cs) | 10.0 |
| (7) | Dimethylcyclopolysiloxane (D5) | 10.0 |
| (8) | Methylparaben | 0.2 |
| (9) | Glycerin | 16.0 |
| (10) | 1,3-Butylene glycol | 3.0 |
| (11) | Purified water | Balance |
|  | Total | 100 |

Example 10

Cream

The cream having the composition as shown in Table 4 was prepared in the below-described process. The cream thus obtained had good stability and a good feeling to the skin upon use (ease of spreading, nonstickiness).
(Preparation Process)

Components (1) to (9) are dissolved at 80° C., followed by stirring uniformly to prepare an oil phase. Components (10) to (13) are dissolved at 80° C., followed by stirring uniformly to prepare an aqueous phase. The aqueous phase is added to the oil phase and the mixture is stirred uniformly at 80° C. Components (14) to (16) are added while cooling the reaction mixture to room temperature, whereby a cream is obtained.

TABLE 4

|  | (Component) | (weight %) |
|---|---|---|
| (1) | Pseudo type ceramide *1 | 7.0 |
| (2) | Pseudo type sphingosine | 0.2 |
| (3) | Myristic acid | 0.25 |
| (4) | Dextrin palmitate | 2.0 |
| (5) | Squalane | 13.0 |
| (6) | Dimethylpolysiloxane (6 cs) | 14.0 |
| (7) | Dimethylpolysiloxane (10 cs) | 5.0 |
| (8) | Methylpolysiloxane.crosslinked Methylpolysiloxane mixture | 1.25 |
| (9) | Paraffin | 0.5 |
| (10) | Extract of *Thujopsis dolabrata* | 1.0 |
| (11) | Eucalyptus extract | 1.0 |
| (12) | Extract of *Fucales fucus* | 1.0 |
| (13) | Methylparaben | 0.2 |
| (9) | Glycerin | 16.0 |
| (10) | 1,3-Butylene glycol | 3.0 |
| (11) | Purified water | Balance |
|  | Total | 100 |

Example 11

Cream

The cream having the composition as shown in Table 5 was prepared in the below-described process. The resulting cream had good stability and a good feeling to the skin upon use (ease of spreading, nonstickiness).
(Preparation Process)

Components (1) to (9) are dissolved at 80° C., followed by stirring uniformly to prepare an oil phase. Components (10) to (13) are dissolved at 80° C., followed by stirring uniformly to prepare an aqueous phase. The aqueous phase is added to the oil phase and the mixture is stirred uniformly at 80° C. The reaction mixture is then cooled to room temperature, whereby a cream is obtained.

TABLE 5

|  | (Component) | (weight %) |
|---|---|---|
| (1) | Ceramide 2 | 5.0 |
| (2) | Ceramide 3 | 0.5 |
| (3) | Ceramide 6 | 0.5 |
| (4) | Phytosphingosine | 0.2 |
| (5) | Myristic acid | 0.3 |
| (6) | Dextrin palmitate | 2.0 |
| (7) | Squalane | 9.0 |
| (8) | Dimethylpolysiloxane (6cs) | 10.0 |
| (9) | Dimethylcyclopolysiloxane (D5) | 10.0 |

TABLE 5-continued

|  | (Component) | (weight %) |
|---|---|---|
| (10) | Methylparaben | 0.2 |
| (11) | Glycerin | 16.0 |
| (12) | 1,3-Butylene glycol | 3.0 |
| (13) | Purified water | Balance |
|  | Total | 100 |

The water-in-oil emulsified composition of the present invention has excellent stability and provides a good feeling to the skin upon use.

The invention claimed is:

1. A process for preparing a water-in-oil emulsified composition, wherein the method comprises
    (1) dissolving under heat the following components (A), (B), and (C):
        (A) a sphingosine represented by the following formula (1):

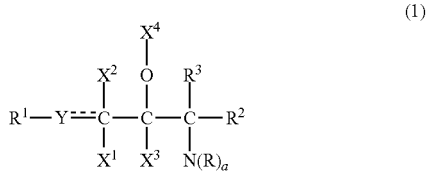

wherein, $R^1$ represents a linear, branched or cyclic, saturated or unsaturated $C_{4-30}$ hydrocarbon group which may be substituted by a hydroxyl, carbonyl or amino group; Y represents a methylene group, a methine group or an oxygen atom; $X^1$, $X^2$ and $X^3$ each independently represents a hydrogen atom, a hydroxyl group or acetoxy group, $X^4$ represents a hydrogen atom, an acetyl group or glyceryl group, or forms an oxo group together with the adjacent oxygen atom wherein, when Y represents a methine group, either $X^1$ or $X^2$ represents a hydrogen atom and the other one does not exist, and when $X^4$ forms an oxo group, $X^3$ does not exist; $R^2$ and $R^3$ each independently represents a hydrogen atom, a hydroxyl group, a hydroxymethyl group or an acetoxymethyl group; R each independently represents a hydrogen atom or an amidino group, or a linear or branched, saturated or unsaturated hydrocarbon group having 1 to 8 carbon atoms in total and optionally having a substituent selected from hydroxyl, hydroxyalkoxy, alkoxy and acetoxy groups; a stands for 2 or 3; and a dashed line indicates a saturated bond or unsaturated bond,
        (B) at least one $C_{12-30}$ fatty acid; and
        (C) an oil component, thereby forming a solution, whereby a sphingosine salt with components (A) and (B) is formed,
            wherein component (A) is present in an amount of 0.005 to 3 wt % based on the weight of the composition, and component (B) is present in an amount of from 0.3 to 5 moles per mole of component (A),
    (2) adding water to the solution, and then
    (3) emulsifying with the sphingosine salt in the absence of a surfactant.

2. A water-in-oil emulsified composition prepared by the process according to claim 1.

3. The water-in-oil emulsified composition of claim 2, wherein Component (A) is a natural type sphingosine represented by formula (3):

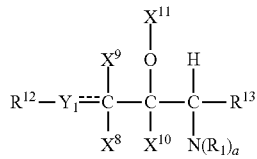

(3)

wherein, $R^{12}$ represents a linear, branched or cyclic, saturated or unsaturated $C_{7-19}$ hydrocarbon group which may be substituted by a hydroxyl group; $Y_1$ represents a methylene or methine group; $X^8$, $X^9$ and $X^{10}$ each independently represents a hydrogen atom, a hydroxyl group or an acetoxy group, $X^{11}$ represents a hydrogen atom or forms an oxo group together with the adjacent oxygen atom, wherein when $Y_1$ represents a methine group, either $X^8$ or $X^9$ represents a hydrogen atom and the other one does not exist, and when $X^{11}$ forms an oxo group, $X^{10}$ does not exist; $R^{13}$ represents a hydroxymethyl or acetoxymethyl group; $R_1$ each independently represents a hydrogen atom or an amidino group, or a linear or branched, saturated or unsaturated hydrocarbon group having 1 to 4 carbon atoms in total and optionally having a substituent selected from hydroxyl, hydroxyalkoxy, alkoxy and acetoxy groups; a stands for 2 or 3; and a dashed line indicates a saturated bond or unsaturated bond; or a pseudo type sphingosine represented by the following formula (4):

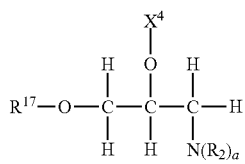

(4)

wherein, $R^{17}$ represents a linear, branched or cyclic, saturated or unsaturated $C_{10-22}$ hydrocarbon group which may be substituted by a hydroxyl group; $X^4$ represents a hydrogen atom, an acetyl group or a glyceryl group; $R_2$ each independently represents a hydrogen atom or an amidino group, or a linear or branched, saturated or unsaturated hydrocarbon group having 1 to 8 carbon atoms in total and optionally having a substituent selected from hydroxyl, hydroxyalkoxy, alkoxy and acetoxy groups, and a stands for 2 or 3.

4. The water-in-oil emulsified composition of claim 2, wherein the oil component is in a solid or semi-solid form.

5. The water-in-oil emulsified composition of claim 2, wherein the oil component comprises a ceramide represented by the following formula (2):

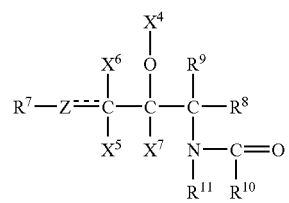

(2)

wherein, $R^7$ represents a linear, branched or cyclic, saturated or unsaturated $C_{4-30}$ hydrocarbon group which may be substituted by a hydroxyl, carbonyl or amino group, or a hydrogen atom; Z represents a methylene group, a methine group or an oxygen atom; $X^5$, $X^6$ and $X^7$ each independently represents a hydrogen atom, a hydroxyl group or acetoxy group, $X^4$ represents a hydrogen atom, an acetyl group or a glyceryl group or forms an oxo group together with the adjacent oxygen atom, wherein when Z represents a methine group, either $X^5$ or $X^6$ represents a hydrogen atom and the other one does not exist, and when $X^4$ forms an oxo group, $X^7$ does not exist; $R^8$ and $R^9$ each independently represents a hydrogen atom, a hydroxyl group, a hydroxymethyl group or an acetoxymethyl group; $R^{10}$ represents a linear, branched or cyclic, saturated or unsaturated $C_{5-60}$ hydrocarbon group which may be substituted by a hydroxyl, carbonyl or amino group and may have an ether bond, ester bond or amide bond in the main chain; $R^{11}$ represents a hydrogen atom, or a linear or branched, saturated or unsaturated hydrocarbon group having 1 to 30 carbon atoms in total and optionally having a substituent selected from hydroxyl, hydroxyalkoxy, alkoxy and acetoxy groups, wherein when $R^7$ represents a hydrogen atom and Z represents an oxygen atom, $R^{11}$ represents a hydrocarbon group having 10 to 30 carbon atoms in total, and when $R^7$ represents a hydrocarbon group, $R^{11}$ represents a hydrocarbon group having 1 to 8 carbon atoms in total; and a dashed line indicates a saturated bond or unsaturated bond.

6. The water-in-oil emulsified composition of claim 2, wherein in formula (1), R' is a linear or branched $C_{10-20}$ alkyl group or a linear or branched $C_{10-20}$ alkyl group having, at a terminal thereof on the Y side, a hydroxyl group.

7. The water-in-oil emulsified composition of claim 6, wherein $R^1$ is selected from the group consisting of tridecyl, tetradecyl, pentadecyl, hexadecyl, 1-hydroxytridecyl, 1-hydroxypentadecyl, isohexadecyl and isostearyl.

8. The water-in-oil emulsified composition of claim 2, wherein at most one of $X^1$, $X^2$ and $X^3$ represents a hydroxyl group, the remaining ones represent a hydrogen atom, and $X^4$ represents a hydrogen atom.

9. The water-in-oil emulsified composition of claim 2, wherein $R^2$ represents a hydrogen atom, a hydroxyl group, a hydroxymethyl group or an acetoxymethyl group, and $R^3$ is a hydrogen atom.

10. The water-in-oil emulsified composition of claim 2, wherein component (A) is present in an amount of 0.01 to 3 wt % based on the weight of the composition.

11. The water-in-oil emulsified composition of claim 2, wherein component (B) is present in an amount of from 0.001 to 10 wt % based on the weight of the composition.

12. The water-in-oil emulsified composition of claim 2, wherein component (B) is present in an amount of from 0.01 to 3 wt % based on the weight of the composition.

13. The water-in-oil emulsified composition of claim 2, wherein component (B) is present in an amount of from 0.5 to 3 moles per mole of component (A).

14. The water-in-oil emulsified composition of claim 2, wherein component (B) is one or more $C_{12-18}$ fatty acids.

15. The water-in-oil emulsified composition of claim 2, wherein component (C) comprises a non-polar liquid oil.

16. The water-in-oil emulsified composition of claim 15, wherein the non-polar liquid oil is present in an amount of 90 wt % or more of component (C).

17. A method of treating the skin comprising applying the water-in-oil emulsified composition of claim 2 to the skin.

* * * * *